(12) United States Patent
Keppel et al.

(10) Patent No.: US 9,028,390 B2
(45) Date of Patent: *May 12, 2015

(54) APPARATUS AND METHOD FOR EXTERNAL BEAM RADIATION DISTRIBUTION MAPPING

(71) Applicant: Hampton University, Hampton, VA (US)

(72) Inventors: Cynthia E. Keppel, Norfolk, VA (US); Paul Gueye, Hampton, VA (US); Christopher Sinesi, Virginia Beach, VA (US)

(73) Assignee: Hampton University, Hampton, VA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/945,167

(22) Filed: Jul. 18, 2013

(65) Prior Publication Data

US 2014/0018675 A1    Jan. 16, 2014

Related U.S. Application Data

(63) Continuation of application No. 12/841,891, filed on Jul. 22, 2010, now Pat. No. 8,568,285, which is a
(Continued)

(51) Int. Cl.
*A61N 5/00*    (2006.01)
*A61B 6/00*    (2006.01)
(Continued)

(52) U.S. Cl.
CPC ........... *A61B 6/425* (2013.01); *A61N 5/1015* (2013.01); *A61N 5/1027* (2013.01); *A61N 5/1048* (2013.01); *A61M 25/10* (2013.01); *A61N 5/10* (2013.01); *G01T 1/1644* (2013.01)

(58) Field of Classification Search
USPC .................. 600/1–8; 250/370.07, 370.11
See application file for complete search history.

(56) References Cited

U.S. PATENT DOCUMENTS

| 5,961,458 A | 10/1999 | Carroll |
| 6,200,255 B1 | 3/2001 | Yu |

(Continued)

FOREIGN PATENT DOCUMENTS

| JP | 03-0257391 | 11/1991 |
| JP | 10-213663 | 8/1998 |

(Continued)

OTHER PUBLICATIONS

Alcón EP, EPR study of radiation stability of organic plastic scintillator for cardiovascular brachytherapy Sr90-Y90 beta dosimetry, Applied Radiation and Isotopes, Feb. 2005, pp. 301-306, vol. 62, Elsevier Ltd.

(Continued)

*Primary Examiner* — John Lacyk
(74) *Attorney, Agent, or Firm* — McGuireWoods LLP

(57) ABSTRACT

An apparatus and method for in vivo and ex vivo control, detection and measurement of radiation in therapy, diagnostics, and related applications accomplished through scintillating fiber detection. One example includes scintillating fibers placed along a delivery guide such as a catheter for measuring applied radiation levels during radiotherapy treatments, sensing locations of a radiation source, or providing feedback of sensed radiation. Another option is to place the fibers into a positioning device such as a balloon, or otherwise in the field of the radiation delivery. The scintillating fibers provide light output levels correlating to the levels of radiation striking the fibers and comparative measurement between fibers can be used for more extensive dose mapping. Adjustments to a radiation treatment may be made as needed based on actual and measured applied dosages as determined by the fiber detectors. Characteristics of a radiation source may also be measured using scintillating materials.

23 Claims, 13 Drawing Sheets

Related U.S. Application Data continuation-in-part of application No. 12/647,920, filed on Dec. 28, 2009, now Pat. No. 8,133,167, which is a continuation of application No. 11/293,161, filed on Dec. 5, 2005, now Pat. No. 7,662,083.

(51) Int. Cl.
*A61M 25/10* (2013.01)
*G01T 1/164* (2006.01)
*A61N 5/10* (2006.01)

(56) References Cited

U.S. PATENT DOCUMENTS

| | | | |
|---|---|---|---|
| 6,320,935 | B1 | 11/2001 | Shinar et al. |
| 6,458,068 | B1 | 10/2002 | Ellard et al. |
| 6,920,202 | B1 | 7/2005 | Dinsmore |
| 7,328,058 | B2 * | 2/2008 | Iwanczyk et al. ............ 600/425 |
| 7,373,197 | B2 | 5/2008 | Daighighian et al. |
| 7,662,083 | B2 * | 2/2010 | Gueye et al. ................... 600/7 |
| 8,133,167 | B2 * | 3/2012 | Gueye et al. ................... 600/7 |
| 8,568,285 | B2 * | 10/2013 | Keppel et al. ................... 600/7 |
| 2002/0001068 | A1 | 1/2002 | Iwanczyk et al. |
| 2002/0131552 | A1 | 9/2002 | Nishizawa et al. |
| 2003/0163016 | A1 | 8/2003 | Testardi |
| 2004/0106840 | A1 | 6/2004 | Kindlein et al. |
| 2005/0101824 | A1 | 5/2005 | Stubbs |
| 2005/0251119 | A1 | 11/2005 | Eaton et al. |
| 2012/0068075 | A1 | 3/2012 | Beddar et al. |

FOREIGN PATENT DOCUMENTS

| | | |
|---|---|---|
| JP | 2002-267754 | 9/2002 |
| JP | 2003-530544 | 10/2003 |
| WO | WO 01/49162 | 7/2001 |

OTHER PUBLICATIONS

Beddar AS, Plastic scintillation dosimetry: optimization of light collection efficiency, Physics in Medicine and Biology, 2003, pp. 1141-1152 vol. 48, Institute of Physics Publishing, United Kingdom.

FLühs D, et al., Direct reading measurement of absorbed dose with plastic scintillators—The general concept and applications to ophthalmic plaque dosimetry, American Association of Physicists in Medicine, 1996, pp. 427-434, vol. 23(3), Medical Physics, US.

Hashimoto M, Measurement of depth dose distribution using plastic scintillator, Nihon Hoshasen Gijutsu Gakkai Zasshi, Nov. 2003, pp. 1424-1431, vol. 59(11), Japan.

Abstract of Hashimoto M, Measurement of depth dose distribution using plastic scintillator, Nihon Hoshasen Gijutsu Gakkai Zasshi, Nov. 2003, pp. 1424-1431, vol. 59(11), Japan.

Archambault, Louis et al., "Plastic scintillation dosimetry: Optimal selection of scintillating fibers and scintillators", Med. Physics, vol. 32, Jul. 2005, pp. 2271-2278.

Notification of Transmittal of International Search Report and Written Opinion of the International Searching Authority, or the Declaration, International Search Report and Written Opinion of the International Searching Authority, all mailed Oct. 9, 2008.

* cited by examiner

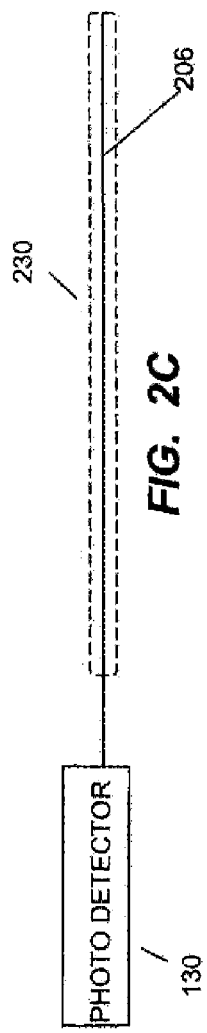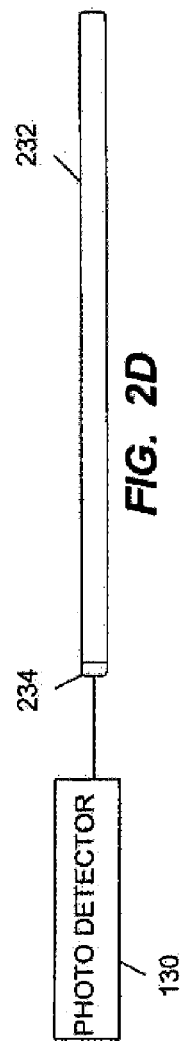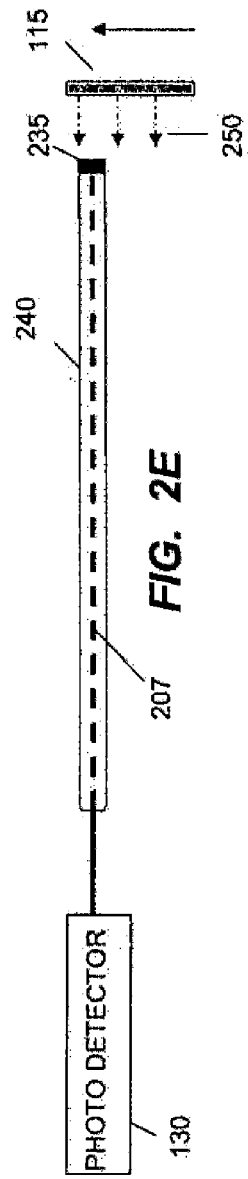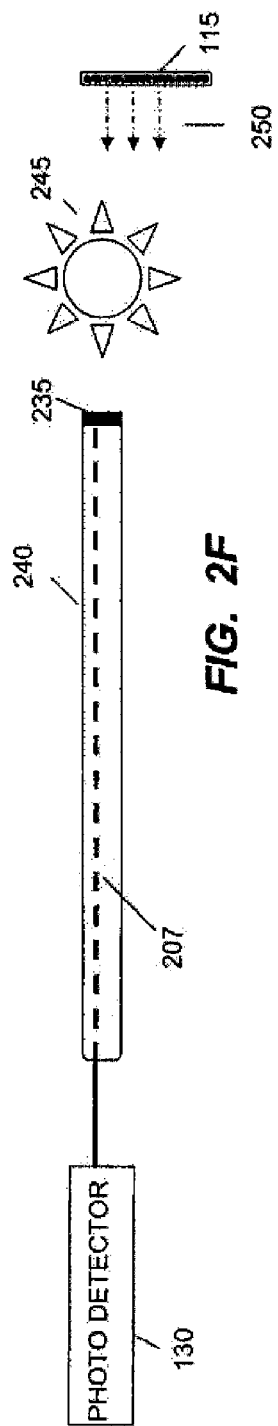

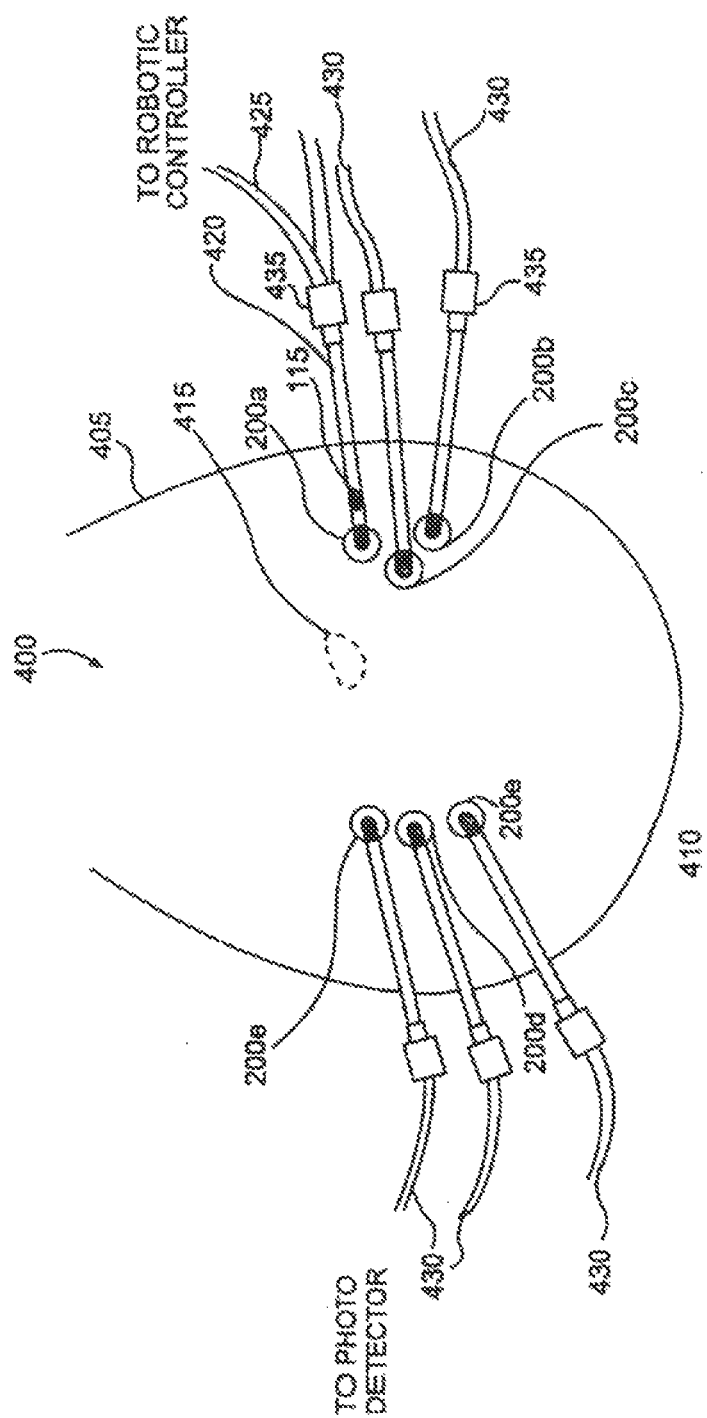

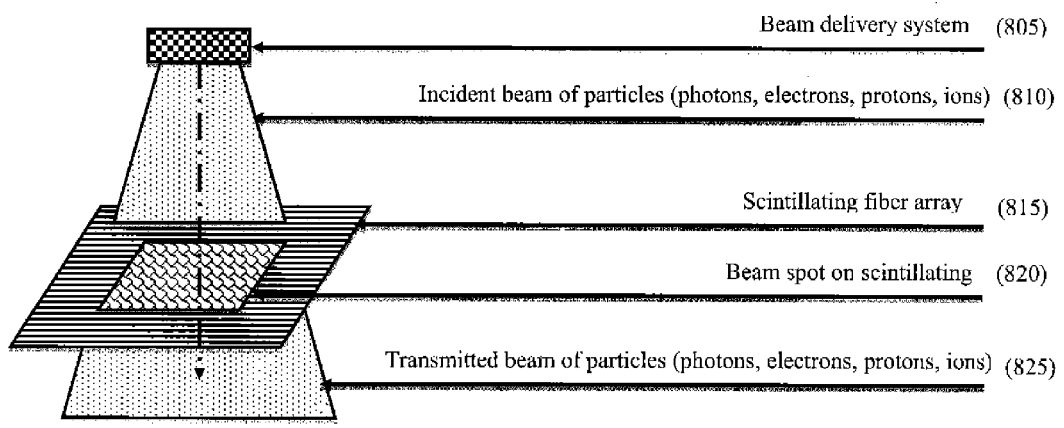
Figure 8: Scintillating fiber material as used for external beam quality assurance system.

Exemplary schematic of a positioning balloon with one or multiple scintillating fibers as an in-vivo or ex-vivo dosimetry monitoring quality assurance system

APPARATUS AND METHOD FOR EXTERNAL BEAM RADIATION DISTRIBUTION MAPPING

CROSS REFERENCE TO RELATED APPLICATIONS

This application is a continuation application of U.S. patent application Ser. No. 12/841,891, filed Jul. 22, 2010, which is a continuation-in-part application of U.S. patent application Ser. No. 12/647,920 filed on Dec. 28, 2009 now issued as U.S. Pat. No. 8,133,167, which is a continuation of U.S. patent application Ser. No. 11/293,161 filed on Dec. 5, 2005 now issued as U.S. Pat. No. 7,662,083, the disclosures of which are incorporated by reference herein in their entirety.

BACKGROUND OF THE INVENTION

1. Field of the Invention

The invention relates generally to detecting radiation levels in radiation therapy and, more particularly, to an apparatus and method for detecting, measuring and altering dosage levels in external beam radiation treatments.

2. Related Art

External beam radiation modalities are the most common treatment and imaging tools for cancer management. In external beam radiation modalities, a beam consisting of photons, electrons or heavier particles (protons are ions) are used to either treat or image cancer tumors. External beam radiation modalities may be used for a wide range of diseases, including, for example, cancer tumors (localized or not localized), assessment of bone structures, and visualization of objects within a body or similar conditions.

Using prostate cancer as an example, there are currently three types of external beam radiation modalities suitable for treating prostate cancer: photon irradiation, proton irradiation and ions irradiation. Each offering various advantages with respect to each other. The patient usually lays on a bed for this treatment and undergoes a two-stage process: an imaging step to assess the location and size of the tumor and a treatment step to eliminate the cancer cells. The first step is primarily performed through the use of photons via X-ray or computerized tomography (CT) scans.

Currently, only post-irradiation techniques are used to provide a crude assessment of the dose delivered to patient in external beam therapy. Recent clinical studies also indicate that some cancers may be caused during the imaging process. There is currently no method for measuring the real-time multi-dimensional tissue dose distribution. Instead, tissue density mapping may be obtained from magnetic resonance imaging and x-ray computed tomography. These tissue density maps are often utilized in combination with the total beam fluency, beam positions and irradiation times, in Monte Carlo simulations to calculate the dose distribution in tissue. However, relying on simulations does not provide any actual measured dose distribution and therefore any over or under exposure is typically determined post therapy by the physiological response. Without ability to measure actual dosage distribution during external beam radiation modalities, adjustments of the dose distribution cannot be made during treatments so that a more desired effect can be achieved such as assuring more effective targeting of tumors, or avoiding/minimizing irradiation of nearby healthy tissue.

Accordingly, there is a need to be able to characterize the radiation beam to aid in creating an external beam radiation treatment plan based on the characterized beam radiation source. Furthermore, there is a need to a have a way to measure actual radiation dosages delivered in external beam radiation modalities when using the characterized beam radiation source to determine tissue dosimetry so that a way of altering the treatment plan, based on the actual measurements, might be achieved. In this way, a desired dosage level and distribution of radiation might be more accurately delivered during the course of treatment.

SUMMARY OF THE INVENTION

The invention satisfies the foregoing needs and avoids the drawbacks and limitations of the prior art by providing an apparatus, system and methods for the characterization of radiation sources used in radiation therapy and imaging and for detecting, measuring and altering dosage levels during treatments and imaging procedures. In particular, the invention provides for in vivo and ex vivo control, detection and measurements of radiation using scintillating materials.

Accordingly, in one aspect of the invention an active delivery or measuring guide, which may be a catheter or other suitable device, is provided. The active measuring guide includes a receptacle for receiving a source of radiation or a radiation beam and at least one radiation detector, including scintillating material, emitting a light level in proportion to sensed incident levels of radiation.

In another aspect of the invention, a system for monitoring brachytherapy or external beam radiation is provided. The system includes a radiation sensing device, which again may be a catheter or other device, having a receptacle for receiving a radiation source or a radiation beam, a photo sensor, such as a photomultiplier, connected to the sensing device and a delivery system connected to the sensing device. The delivery system moves a radiation source or a radiation beam in the sensing device according to a pre-determined plan and the sensing device is configurable for use with the delivery system.

According to another aspect of the invention, a method for characterizing a radiation source or radiation beam for use in radiation therapy or imaging is provided. The method includes the steps of moving at least one of a therapeutic radiation source or radiation beam and a radiation detector in relation to the other, measuring radiation characteristics of the radiation source or radiation beam, and recording the measured radiation characteristics and associating the measured radiation characteristics with the radiation source or radiation beam. Further, the invention may provide a radiation source or radiation beam characterized by this process.

In another aspect of the invention, a method for detecting radiation in brachytherapy or from an external delivery system is provided. The method includes the steps of inserting a radiation source into a delivery guide and/or measuring a level of radiation emitted by a radiation source or radiation beam by detecting light emitted by the active delivery guide or measuring device.

In yet another aspect of the invention, a radiation detector for use in brachytherapy or external beam radiation is provided. The radiation detector includes scintillating material responsive to radiation and configured to be coupled to a photo detector, wherein the scintillating material is implantable in a biological body and the photo detector detects light levels emitted by the scintillating material and provides outputs indicative of radiation levels detected by said scintillating material.

In another aspect, a radiation detector is provided including a catheter having an opening at a first end, and at least one balloon portion coupled to the catheter proximate a second end, wherein the at least one balloon portion includes scintillating material arranged along a surface of the balloon portion, the scintillating material configured to be coupled to a photo detector, for detecting incident levels of radiation in a balloon-related procedure or for adjusting a treatment plan based on the detected level of radiation.

In another aspect, a radiation detector is provided that includes a first set of scintillating fibers, and a second set of scintillating fibers arranged at an angle to the first set of scintillating fibers, wherein at least one first signal from the first set of scintillating fibers and at least one second signal from the second set of scintillating fibers provide an indication of detected levels of incident radiation, a location of the radiation being associated with the intersection of respective first set of scintillating fibers and second set of scintillating fibers producing the respective detected at least one first signal and at least one second signal for adjusting a treatment plan based on the detected level of radiation.

In still another aspect, a method for tracking beam particles is provided that includes providing a first set of scintillating fibers and providing a second set of scintillating fibers arranged at an angle to the first set of scintillating fibers, wherein at least one first signal from the first set of scintillating fibers and at least one second signal from the second set of scintillating fibers provide an indication of detected levels of radiation, a location of the detected radiation being associated with the intersection of respective first set of scintillating fibers and second set of scintillating fibers producing the respective detected at least one first signal and at least one second signal for tracking a beam of the radiation.

In another aspect, a radiation detector is provided that includes at least one positioning device having at least one expandable portion for use in therapy or diagnostic procedures and scintillating material, wherein the at least one positioning device includes the scintillating material arranged along a wall of the at least one expandable portion, the scintillating material configured to be coupled to a photo detector for detecting incident levels of radiation in the balloon-assisted procedure.

In another aspect, a radiation detection is provided including at least one fiber configured with scintillating material along at least a portion of the length of the at least one fiber or configured with scintillating material proximate an end of the at least one fiber, wherein the at least one fiber is positionable to maintain respective scintillating material at a measurement location, and wherein the at least one fiber is configured to be coupled to a photo detector for detecting and measuring incident radiation.

In another aspect, a method for radiation detection is provided that includes providing at least one fiber configured with scintillating material along at least a portion of the length of the at least one fiber or configured with scintillating material proximate an end of the at least one fiber, wherein the at least one fiber is positionable to maintain respective scintillating material at a measurement location, and coupling the at least one fiber to a photo detector for detecting and measuring incident radiation at the at least one fiber for altering a treatment plan based on the detected and measured incident radiation.

Additional features, advantages, and embodiments of the invention may be set forth or apparent from consideration of the following detailed description, drawings, and claims. Moreover, it is to be understood that both the foregoing summary of the invention and the following detailed description are exemplary and intended to provide further explanation without limiting the scope of the invention as claimed.

BRIEF DESCRIPTION OF THE DRAWINGS

The accompanying drawings, which are included to provide a further understanding of the invention, are incorporated in and constitute a part of this specification, illustrate embodiments of the invention and together with the detailed description serve to explain the principles of the invention. No attempt is made to show structural details of the invention in more detail than may be necessary for a fundamental understanding of the invention and the various ways in which it may be practiced. In the drawings:

FIGS. 2C and 2D are schematic diagrams showing embodiments of radiation detectors, constructed according to principles of the invention, with FIG. 2C showing the detector constructed as a scintillating fiber with an optional housing, and FIG. 2D showing the detector made of solid, liquid, or gaseous scintillating material;

FIG. 2E is a schematic diagram of another radiation detector of the invention having scintillating material at its tip and its use in characterizing a radiation source;

FIG. 2F is an illustration of the radiation detector of FIG. 2E being used to detect radiation in vivo, according to principles of the invention;

FIG. 4 is a schematic diagram showing an illustrative example of use of a plurality of active catheters of the invention for treating a tumor, according to principles of the invention;

FIG. 8 is a diagram of an embodiment for external beam quality assurance, configured according to principles of the invention;

DETAILED DESCRIPTION OF THE INVENTION

Figure 1:
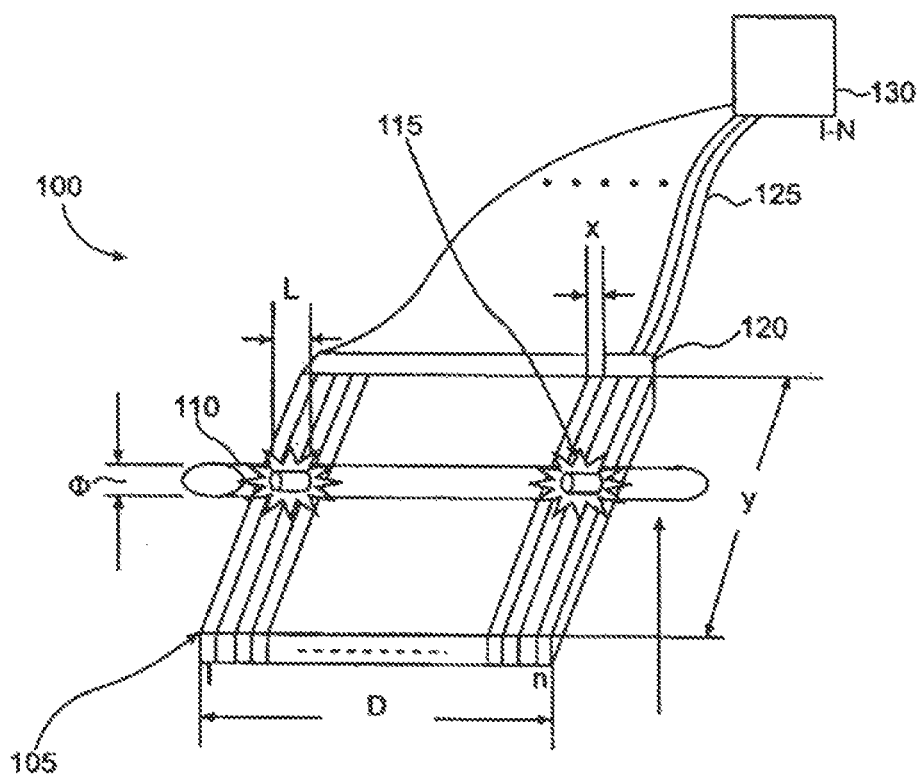
FIG. 1 is a functional block diagram of an apparatus for characterizing radiation sources, constructed according to principles of the invention.

The embodiments of the invention and the various features and advantageous details thereof are explained more fully with reference to the non-limiting embodiments and examples that are described and/or illustrated in the accompanying drawings and detailed in the following description. It should be noted that the features illustrated in the drawings are not necessarily drawn to scale, and features of one embodiment may be employed with other embodiments as the skilled artisan would recognize, even if not explicitly stated herein. Descriptions of well-known components and processing techniques may be omitted so as to not unnecessarily obscure the embodiments of the invention. The examples used herein are intended merely to facilitate an understanding of ways in which the invention may be practiced and to further enable those of skill in the art to practice the embodiments of the invention. Accordingly, the examples and embodiments herein should not be construed as limiting the scope of the invention, which is defined solely by the appended claims and applicable law. Moreover, it is noted that like reference numerals represent similar parts throughout the several views of the drawings.

It is understood that the invention is not limited to the particular methodology, protocols, devices, apparatus, materials, applications, etc., described herein, as these may vary. It is also to be understood that the terminology used herein is used for the purpose of describing particular embodiments only, and is not intended to limit the scope of the invention. It must be noted that as used herein and in the appended claims, the singular forms "a," "an," and "the" include plural reference unless the context clearly dictates otherwise.

Unless defined otherwise, all technical and scientific terms used herein have the same meanings as commonly understood by one of ordinary skill in the art to which this invention belongs. Preferred methods, devices, and materials are described, although any methods and materials similar or equivalent to those described herein can be used in the practice or testing of the invention.

The apparatus and methods of the invention provide for in vivo and ex vivo control, detection and measurements of radiation therapy sources using radiation detectors such as, for example, scintillating material such as scintillating fibers, scintillating crystals, scintillating liquids and scintillating gases. Embodiments of the invention include the apparatus, the use of such apparatus, and methods during the course of patient treatments.

Scintillating material such as fibers have functional properties that convert incident or induced gamma rays into visible light. When a gamma ray photon hits a scintillating fiber, the fiber emits electrons through Compton scattering or the photoelectric effect. As these electrons pass through the scintillating fiber, atoms are excited to a higher state. Light is then emitted as the atom returns to ground state. Similar phenomenon occurs for an incident beam of electrons. The light may then be detected by a detector or photomultiplier tubes with the detected light intensity related to the amount of excitation caused by the radiation source.

FIG. 1 is a functional block diagram of an apparatus for characterizing radiation sources, generally denoted by reference numeral 100. An array of scintillating fibers 105 having a width "D", includes fibers 1-$n$, each fiber having width "x", which may be about 0.2 mm, may be used ex-vivo to characterize a radiation source 115 such as, for example, an iridium-192 seed. The scintillating fiber array 105, also known as an active fiber array, may be coupled to an associated detector(s). The term "active" refers to being responsive to radiation such as emitting light. The radiation source 115 is typically inserted into a radiation delivery guide shown here as catheter 110, usually plastic, having a diameter of "Φ", which may be sized approximate the width of the fiber, which in this example is about 0.2 mm. Of course, other structures may be used as radiation delivery guides. Some examples of other suitable structures are described below. The catheter 110 may be positioned next to the scintillating fiber array 105 with the long axis of the catheter 110 perpendicular to the long axis of the fibers 1-$n$ of scintillating fiber array 105. The radiation source 115 having length "L", which may be about 1 mm, is typically pushed through catheter 110, traversing width "D", which may be about 30 cm, of the scintillating fiber array 105. The dimensions indicated for "x", "Φ", "D" and "L" are exemplary and may vary as necessary for particular applications.

FIG. 1 also illustrates the movement of the radiation source by showing the same radiation source 115 in two different positions, although the radiation source typically has multiple positions as it is stepped across the entire scintillating fiber array 105, which in some embodiments may be an array of other scintillating material. The radiation source 115 may be pushed through the catheter 110 using a delivery system such as a conventional robotically controlled stepping motors (i.e., robotic controller), for example, which may push the source 115 across the array in predetermined increments. Examples of such robotic controllers are GammaMed 2i, Nucletron Corporation's Selectron and Varian Medical System's Vitesse HDR Brachytherapy afterloaders.

As the radiation source 115 traverses the scintillating array 105, the characteristics of the radiation source 115 and its directional intensity may be measured by the photo detector 130. The photo detector 130 may include photo detecting devices such as photomultiplier tubes, photodiodes, charge-coupled devices (CCDs), solid state photomultipliers (SSPMs), or other devices known in the art to detect the transmitted light from the scintillating array 105 induced by the radiation source 115.

In this way, the radiation source 115 may be characterized as to its directionality and intensity in one or more dimensions and over the length of the radiation source 115. Since the radiation source may have variations in characteristics along its length, identifying these variations may now be captured as it moves across the fiber array 105. The unique radioactive properties of the radiation source 115 may then be captured by a computer for subsequent use in developing or executing a treatment plan using the characterized radiation source 115.

The photo detector 130 may be coupled, either permanently or detachably, to each fiber 1-$n$ of the fiber array 105 or by optional light guides 125 which may be securely restrained by restraint 120. Other techniques for coupling scintillating fibers to a photo detector are known by those skilled in the art and which may be used in the invention. For example, photo detectors may be coupled to both ends of the fibers 1-$n$.

In other embodiments, another fiber array or arrays (not shown) may be employed either in one or more planes such as above the catheter 110 and parallel to the fiber array 105 or in a pre-determined plane at an angle to the fiber array 105, to acquire intensity readings of radiation source 115 in multiple orientations for mapping the distribution of radiation from source 115. The distribution and intensity mapping may be captured and recorded, perhaps automatically by computer, for use in development of a treatment plan for a patient. Moreover, the radiation source may be turned (i.e., rotated), typically about its long axis by a known amount, and the characterization process repeated in order to ascertain radiation properties in the new orientation. The characterization of the radiation source may be recorded for later use in treatment planning and treatment application.

The fibers 1-$n$ are typically sized to about 0.2 mm in diameter or width (but may vary), since fiber size determines, in part, spatial distribution and provides for center-of-gravity type calculations of the radiation source 115. The fibers 1-$n$ may have a square, elliptical or circular cross section, and are often formed of a plastic scintillating material. One suitable type of commercially available scintillating fiber that may be used in the invention is known as Bicron BCF-12.

The total width "D" of the fiber array 105 should be sufficient to test for the radiation source 115 uniformity and to test for dwelling positions. Often, in embodiments, "D" may be greater than or equal to 100 L, however, length "D" may be any size that renders an effective reading of dwelling positions for radiation source 115. The length "y" of the fibers 1-$n$ should be greater than the diameter "$\Phi$" of catheter 110. Once the characterization of radiation source 115 has been determined, this information concerning the radiation source 115 may be used to construct a treatment regimen specific to a particular patient so that placement of the radiation source for producing predictable radiation dosages and directionality might be achieved during the course of treatment.

Dwelling positions are positions where the source typically remains stationary for some small period of time. During treatment the sources typically do not move continuously but step, dwell, step, dwell, etc., as needed. So, there is greater radiation delivery at the dwell positions even for a nominal uniform source. Accordingly, if dwell characteristics are known, both the source distribution and the delivered source distribution can be obtained, according to the principles of the invention. Characterization typically refers to the spatial distribution of the intensity at the surface of the source and away from the source (i.e., in the medium where the source is placed). For example, if a dose is prescribed to be delivered to certain area for treatment, for instance, the characterization of the source permits improved dose delivery accuracy and also dose area distribution accuracy.

In order to detect and measure actual radiation dosage during the course of radiation therapy treatments, such as for tumors in the breast or prostate, for examples, an embodiment of a scintillating fiber array may be employed in vivo as a detector array. A scintillating fiber array may be configured to conform to the structure of a catheter, typically circular but may be any configuration according to the catheter, and either embedded in the walls of the catheter or configured to line the inner (or even outer) surface of the catheter.

Figure 2A:
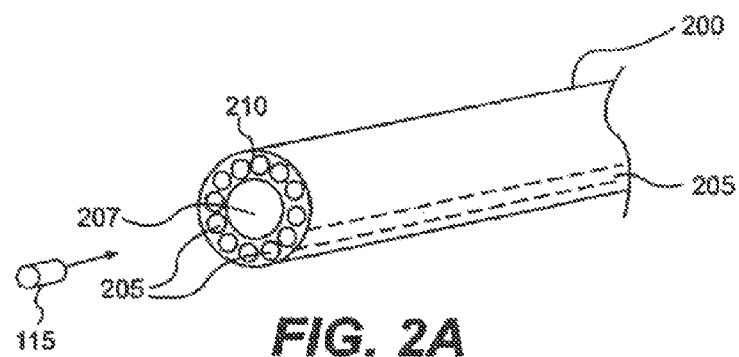
FIGS. 2A and 2B are schematic diagrams showing embodiments of active catheters, according to principles of the invention.
Figure 2B:
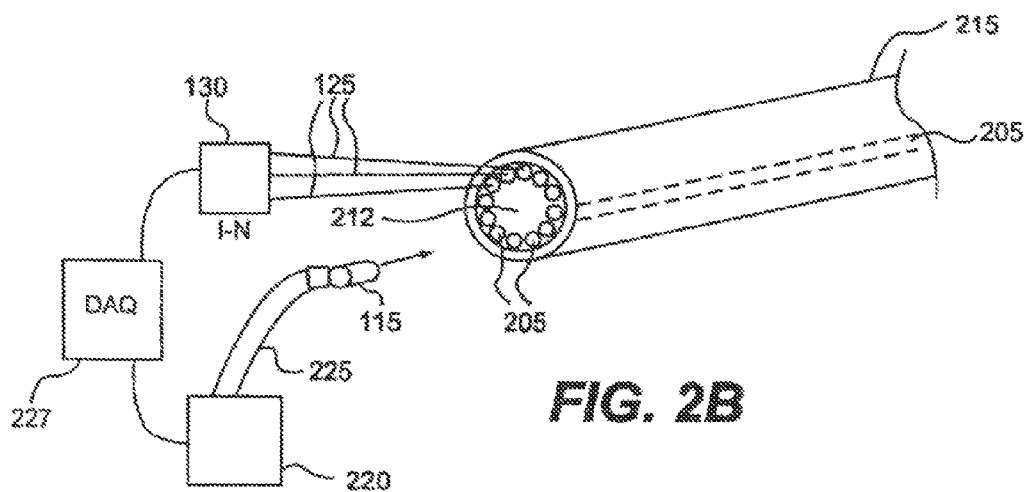

FIGS. 2A and 2B schematically illustrate embodiments of active catheters of the invention. The active catheter or other implantable medical device is capable of sensing radiation levels and delivering outputs to a photo detector. Referring to FIG. 2A, active catheter 200 may be constructed with a plurality of scintillating fibers 205 embedded or otherwise arranged in the walls 210 of the catheter 200. The number of scintillating fibers 205 may be such that they substantially encompass the inner circumference of the catheter 200, however, a fewer number of fibers may be employed. The length of scintillating fibers 205 may have a length substantially the same as the length of catheter 200, or the length of the catheter that the source 115 traverses, but may be longer as necessary for connecting to a photo detector, for reasons described below. The diameter or thickness of the scintillating fibers 205 may be as small as about 100 µm, or sized as necessary, to line the circumference of the catheter 200 with multiple fibers, preferably four or more fibers.

In other embodiments, some of which are described below in more detail, the catheter may be solely a radiation detector with one or more scintillating fibers, but without a shaft for receiving a radiation seed. This shaft-less catheter may be deployed in vivo as a detector mechanism. The shaft-less catheter may have smaller overall dimensions as compared with a catheter configured with a shaft.

Optionally, optical fibers, light guides or wave guides may be attached to the end of each scintillating fiber 205 to provide signals to a photo detector, photomultiplier or similar device while also permitting controlled insertion of a radiation source 115 into the inner chamber 207. However, the scintillating fibers may be coupled to a photo detector directly. Examples of suitable photo detectors include photomultipliers (PMT) from Hamamatsu such as the C8 multi-anode PMT and Centrovision series 5-T photodiodes.

Referring to FIG. 2B, the active catheter 215, has a plurality of scintillating fibers 205 arranged into a substantially circular array which may be constructed as an independent component and inserted into the catheter 215 formed integrally with the inner circumference, or affixed in any other manner known in the art. Preferably, if a small number of scintillating fibers are employed, then the spacing should be evenly distributed. The circular array may be bonded and held in an essentially circular orientation by an appropriate flexible adhesive or by a thin adhesive faced backing. In other embodiments, the inner surface of the catheter may have sleeves along its length, or part of its length, to receive removable or non-removable lengths of scintillating fiber. Moreover, the plurality of scintillating fibers 205 may be embedded in the walls of the active catheter 215, perhaps substantially equally spaced about the circumference of the active catheter 215.

As noted above, the diameter or thickness of the scintillating fibers 205 may be as small as about 100 µm, or sized as necessary, to line, at least partially, the circumference of the catheter 200 with multiple fibers, preferably four or more fibers. The shape of the scintillating fibers may be essentially any shape including circular, elliptical, square, etc. Optional photo or wave guides 125, as shown in FIG. 2B, may be attached to the end of each scintillating fiber 215 to provide signals to a photo detector or photomultiplier 130 while also permitting controlled insertion of a radiation source 115 into the inner chamber 212. The fiber 205 may be coupled directly to a photo detector without the use of a light or wave guide.

The radiation source 115 may be inserted into a receptacle of the catheter 215 and controlled via a lead 225 by a conventional robotic stepping motor apparatus 220. The stepping control lead 225 and optional wave guides 125 may be combined into a common harness and attachment assembly for ease of use. The robotic controller 220 provides stepping movement of the radiation source 115 in predetermined increments, according to pre-determined programming. Further, in some embodiments, the robotic controller 220, under suitable program control, may provide rotational control of the radiation source 115 to alter its orientation about its longitudinal axis (during stepping and/or when stopped).

Further shown in FIG. 2B is a data acquisition system (DAQ) 227 for receiving outputs from the photo detector 130 and for interacting with the robotic controller 220 such as for receiving outputs and/or for controlling the robotic controller. The DAQ 227 may also provide data storage, display components and computational processing, such as Bracytherapy Dose Monte Carlo algorithms to reconstruct applied radiation by projecting a dose map, as described below.

FIG. 2C is an embodiment of a radiation detector constructed as a scintillating fiber with an optional housing, according to principles of the invention. The radiation detector 230 is formed by scintillating material 206 encased in an optional housing 230 that provides either flexible protection or rigid protection to the scintillating material 206 and/or permits the scintillating material to be implantable in vivo, e.g., in a manner similar to the active catheter embodiments described above. The scintillating material 206 may be a scintillating fiber and may be suitable for in vivo use without any encasing structure such as the housing 230. Moreover, the scintillating material 206 may be operatively coupled to a photo detector 130.

FIG. 2D is another embodiment of a radiation detector made of solid, liquid or gaseous scintillating material, according to principles of the invention. The radiation detector 232 is formed from a scintillating material such as, for example, scintillating gas (with an encasement encasing the gas), scintillating crystals, scintillating liquid (with an encasement encasing the liquid) or other scintillating solid. The radiation detector 232 may be implantable in vivo, like the active catheter embodiments, and may be operatively coupled 234 to a photo detector 130.

FIG. 2E is yet another embodiment of a radiation detector having scintillating material at its tip, which shows its use in characterizing a radiation source, according to principles of the invention. The radiation detector 240 has an end portion 235 including scintillating material coupled to an optical fiber 207 (or, alternatively, a light guide) which is connectable to a photo detector 130. In alternate embodiments, the scintillating material may be directly coupled to a photo detector. This radiation detector 240 may be somewhat more discriminating as a detector since only the tip of the detector is responsive to radiation 250. Further, the radiation detector 240 may be employed to characterize a radiation source 115 by moving a radiation source 115 in a perpendicular direction to the detector 240. Alternatively, the detector 240 may be moved while the radiation source is stationary. In this way, the radiation source 115 may be characterized in a manner similar to the manner described in relation to FIG. 1. The radiation detector 240 may also be implantable in vivo to measure radiation levels during treatments. Furthermore, the radiation source 115 may be characterized in a similar fashion using the radiation detector embodiment of FIG. 2C, which has a single scintillating fiber. For example, the scintillating fiber detector of FIG. 2C may be oriented with the end of the scintillating fiber towards the radiation source (i.e., perpendicular to the radiation source in a similar manner to that shown in FIG. 2E) and to characterize the radiation source by moving either the scintillating fiber or the radiation seed.

FIG. 2F is an illustration showing how the radiation detector of FIG. 2E may be used to detect radiation in vivo, according to principles of the invention. FIG. 2F shows the radiation detector 240 having a scintillating material end portion 235 and optical fiber 207 connected to a photo detector 130. When placed in vivo near a tumor 245, the detector 240 detects radiation 250 such as emitted by a radiation source 115. The radiation source 115 may be placed in vivo by the active catheters of FIGS. 2A and 2B, for example. The radiation detector 240 then detects a level of radiation 250, which may be attenuated by the tumor 245. The level of light measured by the photo detector 130 is indicative of radiation levels detected at the end portion 235, which may then be used to reconstruct or confirm actual applied radiation dosage during a treatment, as discussed below. Of course, multiple radiation detectors 240 might be employed simultaneously in vivo in order to construct a more detailed dosage map as a result of a treatment. In alternate embodiments, a fiber optic 207 and the scintillating materials 235 may be constructed so that the combination of the two forms a radiation detector without any other outer structure.

Figure 3:
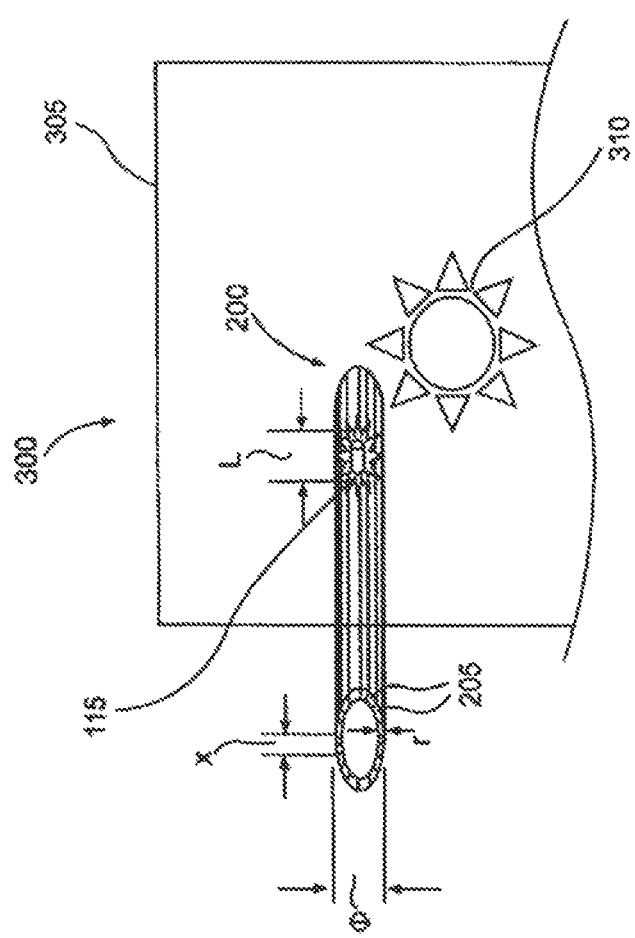
FIG. 3 is schematic diagram showing an illustrative example of use of an active catheter of the invention in a biological system, according to principles of the invention.

FIG. 3 illustrates use of an active catheter of the invention in a biological system, generally denoted as reference numeral 300. Biological system 300, which may be a part of a subject such as a human or an animal, is shown with a tumor or plaque mass 310 requiring radiation therapy treatment. The active catheter 200 (or, alternatively, 215) may be implanted in a biological system 300 to irradiate the tumor 310 according to a pre-determined radiation treatment plan based on radiation source 115 characteristics, as determined in accordance with the principles explained with reference to FIG. 1, for example. The radiation treatment plan may occur over the course of several treatments, perhaps over days or weeks. The placement of the active catheter 200 into the biological system 305 facilitates measuring data of actual radiation dosage applied.

The scintillating fibers 205 used in FIG. 3 may have a width "x" different from height "r". The diameter "Φ" must be sufficiently large as to receive the radiation source 115 and robotic stepper control lead 225 in order to move the radiation source along the length of the active catheter 200, or the guide path therein. A photo detector and stepping controller are not shown in FIG. 3, but are typically present, as previously discussed in relation to FIG. 2B.

The robot stepping controller (e.g., 220) is usually calibrated so that the beginning position (one end of active catheter 200) of the radiation source 115 is known, as well as the total length to traverse in the active catheter 200. As the stepping controller 220 moves the radiation source through the active catheter 200, the position may be constantly calculated, or derived from known techniques, since the distance per step is known.

However, the nature of the active catheter 200 may also provide another feature, i.e., it may function as a calibration and tracking mechanism to assure the location of the radiation source 115 during its transit through the active catheter 200, in addition to its function of detecting the dosage emitted by the radiation source 115. As the radiation source 115 traverses active catheter 200 under control of the robotic controller, each of the scintillating fibers 205 senses the emission of radiation and generates light in proportion to the intensity of the radiation, with the signal at the photo detector weakening with distance from the source in a calibratable and repeatable way.

However, as the radiation source 115 moves along the catheter 200, the apparent intensity of the generated light in each fiber diminishes since the light must traverse greater distances through the scintillating fibers to reach a photo detector that is typically coupled to each end of the scintillating fibers 205, i.e., effectively attenuating the light signal. This attenuation rate or level is related to the distance traversed by the radiation source 115 in the active catheter 200 and, when calculated, should substantially match with a current position known by the robotic controller 220, typically based on pre-determined steps or increments. If a discrepancy occurs between positions as calculated and established by the robotic stepping motor as compared with calculated positions based on the scintillating fiber(s) light levels, corrective action may be warranted, perhaps even suspension of treatment. This constant feedback loop and cross-verification between the two location tracking techniques provides added integrity and safety margins to therapy treatment sessions.

As the radiation source 115 traverses the active catheter 200, the intensity of the radiation emitted at any point along the active catheter 200 may also be detected and computed since each scintillating fiber emits light in proportion to the radiation intensity impacting each fiber. This information may be recorded for later simulation to re-create an overall three-dimensional exposure and dosage map of the affected site. Over the course of several treatments, an accumulative dosage map may be generated, perhaps from several radiation detectors, which may provide a basis for adjusting directionality or dosage levels in order to achieve a pre-determined exposure plan of the tumor area under treatment.

Moreover, the dwelling of the radiation source 115 may be corroborated with the robotic stepping controller in real-time to assure that radiation exposure times, hence radiation dose, at any given location along the active catheter 200 is being applied according to the pre-determined treatment plan. In some embodiments, a computer controller (not shown) may be employed to accept outputs from the active catheter 200 (and/or associated photo detector), to process the outputs for generating dosage mapping and to alter and/or control the actions of the robotic controller 220, when necessary, to achieve changes to the treatment, perhaps dynamically.

Generally, known Monte Carlo code (i.e., software and algorithms) describes the interaction of radiation with matter. Because these interactions are probabilistic in nature, a significant number of interactions are usually simulated to obtain the most likely set of interactions for any specific circumstance. Hence, the term "Monte Carlo."

There are two distinct Monte Carlos employed directly or indirectly by the invention. The first is based upon the commercially available programs used commonly for radiation treatment planning. For example, a physician specifies an amount of radiation needed and location and the medical physicist runs this type of Monte Carlo, which simulates the patient dosage. This treatment planning simulation typically requires patient data input such as from a computed tomography (CT) scan, or the like, as well as input describing the radiation source to be used (e.g., external beam, brachytherapy seed, brachytherapy HDR source, etc.) and its characteristics. Examples of this "treatment planning" type of commercially available Monte Carlo packages include Varian's Eclipse or Brachyvision products.

Another type of Monte Carlo, referred to as the "Brachytherapy Dose Monte Carlo," is provided by the invention. The Brachytherapy Dose Monte Carlo is based on the commonly available tool kit, GEANT4, from CERN (European Laboratory for Particle Physics, Geneva, Switzerland) and provides, in part, fast processing for removing the physics processes in the data acquisition such as, for example, data obtained from the outputs of the scintillating detectors of the invention during a treatment. The Brachytherapy Dose Monte Carlo may be used to take into account any radiation scattering during the treatment so that improved image resolution of the measurements might be achieved. The Brachytherapy Dose Monte Carlo also provides a projected dose map within a given area (e.g., to track events back in time). The projected dose map may then be feedback (as input) to the treatment planning Monte Carlo for treatment alterations. The Brachytherapy Dose Monte Carlo may also simulate treatment planning for verification or other purposes.

FIG. 4 illustrates a system showing the use of a plurality of active catheters of the invention for treating a tumor, generally denoted by reference numeral 400. The system 400 is used to treat a body part 405 and a tumor 415 to be treated by radiation therapy. A plurality of active catheters 200a-200e is implanted in a pre-determined orientation in relation to the tumor 415 in anticipation of both applying radiation treatment and also for measuring the actual radiation dosage applied. Any number of active catheters may be employed in any appropriate orientation as deemed appropriate for an intended treatment plan. The location and orientation of the active catheters 200 may be pre-determined by simulation in order to achieve a desired radiation distribution and/or dosage levels deemed appropriate to the diagnosis. The orientation may also be based, at least in part, on the characteristics of a chosen characterized radiation source or sources. The active catheter orientation (and distance relationships) may be confirmed by X-ray or other imaging technique. The same radiation source or other radiation sources may be used simultaneously or serially in one or more of the active catheters 200, as necessary.

In the illustrative example of FIG. 4, one active catheter 200a facilitates delivery of a radiation source (e.g., characterized radiation source 115 of FIG. 1 or 2E) via a combined assembly 420. The combined assembly 420 is configured to permit a stepping robot lead 425 to insert a radiation source into the active catheter 200 while also permitting the output of the active catheter's 200a scintillating fibers (within the active catheter 200a) to traverse the one or more optional light or wave guides 430 to a photo multiplier or other detector (not shown). The one or more optional light or wave guides 430 may be functionally connected to one or more scintillating fibers within active catheter 200. The optional light or wave guides 430 may be a pre-fabricated assembly of multiple wave guides for ease of use. A coupler 435 may also be employed for attaching a robotic controller 425. In some embodiments, the scintillating fibers may be coupled directly to a photo detector without use of the light or wave guide. Moreover, the photo detector and/or robotic controller may be interfaced with a data acquisition system (e.g., DAQ 227 of FIG. 2B)

As the radiation source 115 enters active catheter 200a, a synchronization of the stepping robotic controller and the scintillating fiber output from the active catheter 200a may be performed. In this manner, a cross-check of actual location of the radiation source may be achieved throughout its traversal of the active catheter 200a, as previously described. Further, a baseline reading from each active catheter 200b-200e, and each scintillating fiber therein, may also be established.

As the radiation source 115 traverses the active catheter 200 according to a pre-determined treatment plan that projects an intended dosage amount, each active catheter 200a-200e responds to the effects of the radiation source 115. Each active catheter's 200a-200e response level is dependent on its relationship to the radiation source 115. Of course, active catheter 200a typically responds with an indication of greatest intensity (i.e., greater light level than the other catheters) since the radiation source 115 is in closest proximity by being in catheter 200a. However, based on orientation and distance, each of the other active catheters 200b-200e also supplies an indication of radiation levels (i.e., light levels) which are propagated to a photo detector.

As a treatment progresses, the real-time dose distribution readings from each active catheter may be captured and processed by a data acquisition system (such as DAQ 227 of FIG. 2B) including Brachytherapy Dose Monte Carlo simulation, or similar techniques, to compare against a forecasted expectation. In some embodiments, the data acquisition system may also receive outputs from the robotic controller and may control the operation of the robotic controller based on real-time events. The active catheters 200a-200e provide actual measurements of dosage levels applied to the tumor 415 and the surrounding tissue areas. This measurement provides a greater degree of confidence that a treatment is delivering or has delivered the expected amount of radiation to a site and provides a basis for adjusting subsequent applications as needed over time to achieve the goals of the treatment plan.

The total dose (i.e., total integrated signal) from each catheter determines the total dose seen at a given location (i.e., an active catheter). Knowing the fiber locations inside a patient plus the total dose gives information for 2-dimensional or 3-dimensional dose maps when combining all fibers (which depends on the number of active catheters employed).

If necessary, an additional active catheter 200 may be used in subsequent treatments, or a re-positioning of an active catheter 200 may be warranted based on measured results. Moreover, the radiation source 115 may be applied in any of the active catheters 200, in any order, including simultaneously using additional radiation sources, to achieve a desired overall radiation treatment effect. In other embodiments, the radiation source may also be turned/rotated by the robotic controller to control directionality of the radiation emission.

Figure 5A:
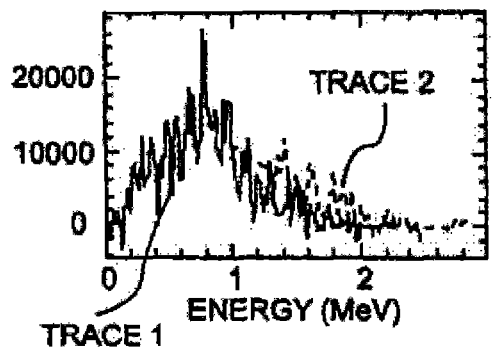
FIGS. 5A-5F are graphs, each graph being illustratively representative of radiation detected by a separate active catheter of the invention from among six active catheters employed during a radiation therapy treatment, according to principles of the invention.
Figure 5B:
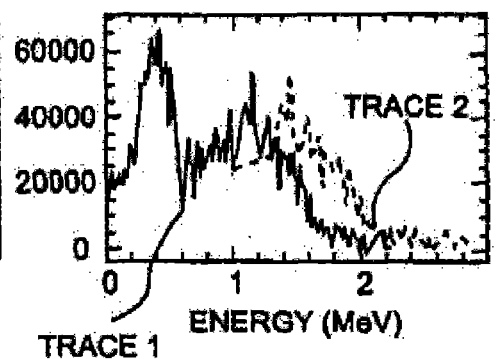
Figure 5C:
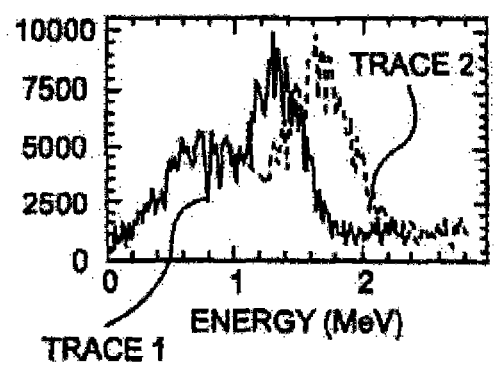
Figure 5D:
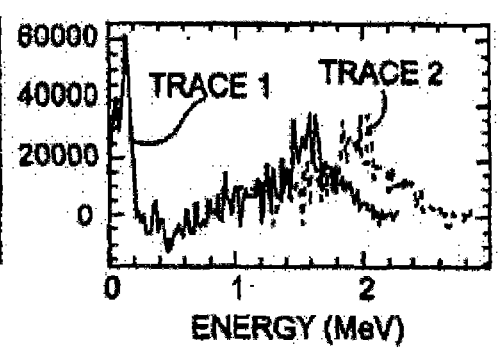
Figure 5E:
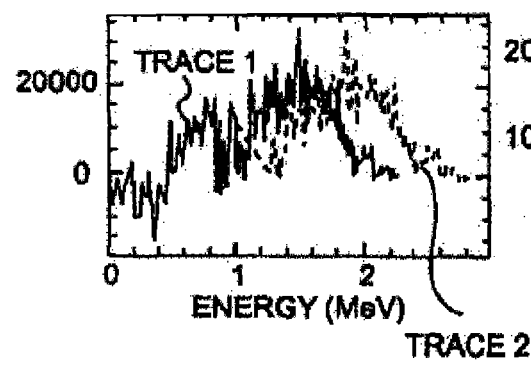
Figure 5F:
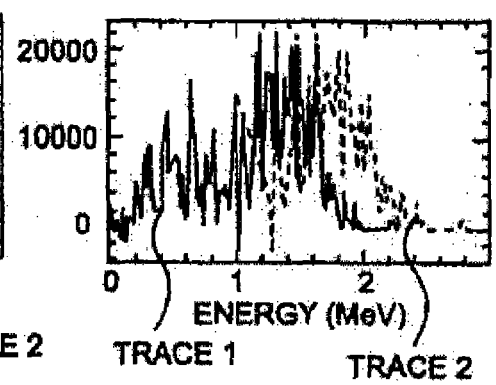

FIGS. 5A-5F are graphs, with each graph illustratively representative of radiation detected by a separate active catheter from among six active catheters that could be employed during a treatment, such as catheters 200a-200e of FIG. 4. FIG. 5A corresponds to a first active catheter used in a treatment; FIG. 5B corresponds to a second active catheter used in a treatment, and likewise for FIGS. 5C through 5F which correspond to active catheters three through six.

The y-axis denotes radiation levels, for example in curies, and represents the number of photons collected by the photo detector (e.g., PMT). The x-axis denotes energy in MeV (million electron volts). Each graph, for each active catheter, shows two traces. The first trace shows the dosage detected at the corresponding active catheter, prior to any correction applied to a treatment plan (e.g., after a first radiation treatment). The information from the first trace (i.e., data from the corresponding active catheter), may be processed by Brachytherapy Dose Monte Carlo simulation or similar simulation in order to correct for physics processes of the treatment. The first trace is indicative of intensity, from the corresponding active catheter's position, of the real-time patient dose, prior to correction.

The Brachytherapy Dose Monte Carlo simulation algorithm uses, at least minimally, relevant physics processes such as Compton scattering, and sufficient speed to produce timely results, for example, in a few minutes, perhaps faster. The Brachytherapy Dose Monte Carlo simulation produces accuracy in location and geometric information of the dosage source, typically accurate to within a few millimeters. Using the data from the multiple active catheters, the Brachytherapy Dose Monte Carlo simulation forms a volumetric dose distribution effectively producing a radiation map. This dose distribution may be used to both monitor patient dose and as input in real time to alter treatment progress and planning.

Trace 2 of each FIG. 5A through 5F illustratively represents the energy distribution of the particles emitted from the source at the surface of the source which provides information on what has been emitted by the source effectively. The trace information may also be used to extrapolate the dose within the patient (after correcting for energy loss and taking into account secondary particles produced).

Based on Brachytherapy Dose Monte Carlo simulation, it may be deemed appropriate to increase a dwell location time period of the radiation source in one or more of the active catheters to achieve an increase (or alternatively, a decrease) in applied radiation dosage in a particular dimension or dimensions. This may translate into the increase (or decrease) in total radiation at a specific site, typically the tumor under treatment, but may also alter delivered dosage to surrounding tissue, as desired.

Real-time capturing or collecting of the active catheter outputs and rapid processing of the detected radiation levels (i.e., corresponding light levels) by the acquisition system (DAQ) provides a rapid feedback tool to radiologists or doctors to authenticate actual dosage levels delivered for a treatment. The fast DAQ system typically includes dedicated algorithms to analyze and present data collected and includes code that converts collected signals to effective dose at the surface of each fiber (or scintillating material). The DAQ system may also perform the Brachytherapy Dose Monte Carlo reconstruction simulations. By comparing a pre-determined treatment plan and its projected radiation distribution to the real-time data acquisition system generated from actual measured radiation levels, a basis is now available to modify placements of the active catheters, change dwelling times/rate of the radiation source movement or change orientations of the radiation source, as necessary, to either decrease or increase radiation levels or directionality of the radiation.

Figure 6A:
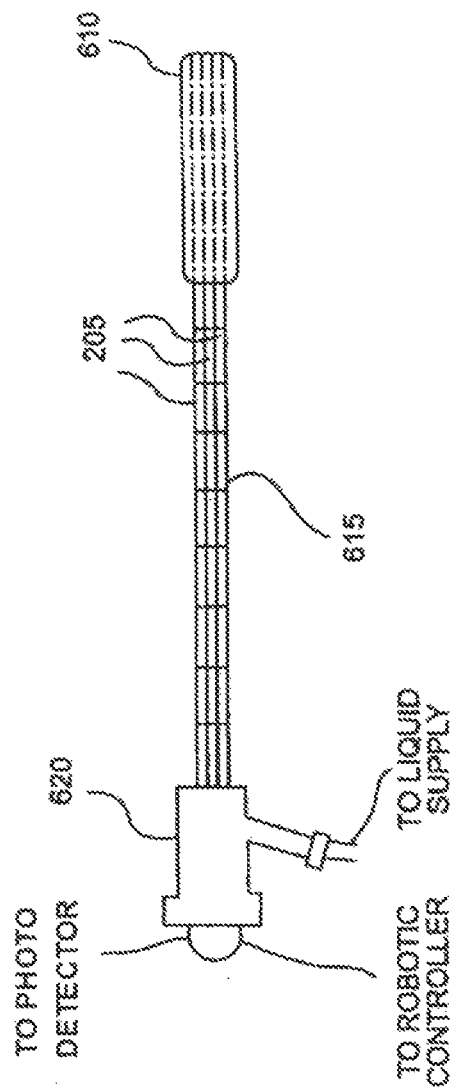
FIG. 6A is a schematic diagram of an active mammosite catheter constructed according to the principles of the invention.

FIG. 6A is a diagram of an active mammosite catheter, generally denoted by reference numeral 615. The active mammosite catheter 615 includes one or more scintillating fibers 205 (the scintillator) arranged along the length of the shaft of the active mammosite catheter 615. The scintillating fibers may be embedded in the walls of the active mammosite catheter 615. The active mammosite catheter 615 also comprises an expandable balloon 610 connected to an end section of the active mammosite catheter 615.

The active mammosite catheter 615 further comprises a coupling section 620 for coupling to a liquid supply for expanding the balloon 610, for operatively connecting to a robotic controller (not shown) for inserting a radiation source (not shown) and for operatively connecting the scintillating fibers 205 to a photo detector (not shown) for detecting light levels emitted by the scintillating fibers 205 when exposed to a radiation source. The scintillating fibers 205 detect radiation signals from the radioactive source when inserted, with a change in signal size dependent on the location within the shaft of the radioactive source. Moreover, signals from the radioactive source within the balloon are similarly reconstructable as a function of distance from the scintillator.

Figure 6B:
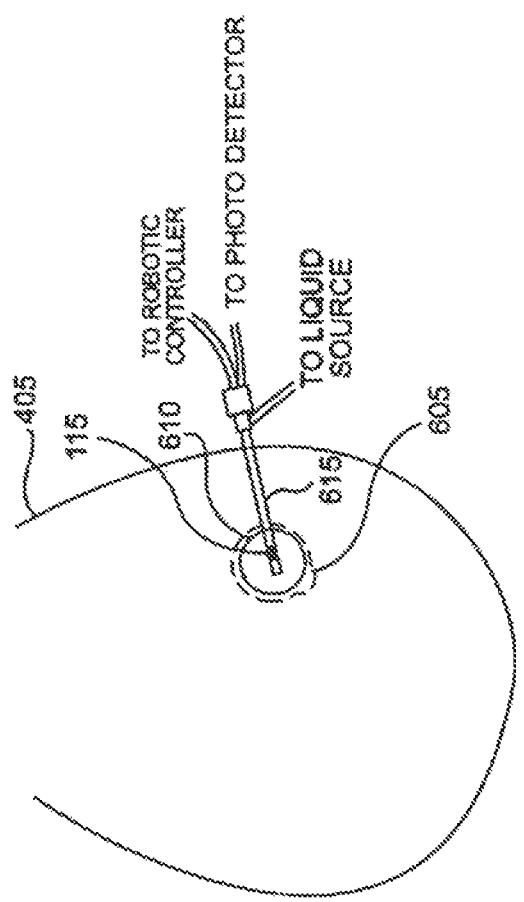
FIG. 6B is a schematic diagram showing an illustrative example use of an active mammosite catheter, according to principles of the invention.

FIG. 6B is an illustrative diagram showing the use of an active mammosite catheter of the invention. As illustrated, a lumpectomy cavity 605, created when a tumor is removed by lumpectomy, is treated with HDR using an active mammosite catheter or mammosite delivery device.

The active mammosite catheter 615 includes expandable balloon 610, shown inserted into a lumpectomy cavity 605. The active mammosite catheter 615 provides delivery of a radiation source 115 through the shaft of the active mammosite catheter 615 into the balloon area, when inflated by a saline solution, for expansion of the attached balloon 610 in cavity 605. The active mammosite catheter 615 outputs, from the scintillating fibers within the active mammosite catheter 615, may be coupled to a corresponding photo detector, as discussed previously in reference to FIG. 2B. A robotic controller lead 620 provides for insertion control of the radiation source 115 and controls pre-determined stepping motion of the radiation source 115. Since the radiation source 115 is insertable through the shaft of the active mammosite catheter 615 to an area within the balloon 610, radiation is delivered to the area where cancer is most likely to recur, the surrounding tissue forming the cavity 605. The active mammosite catheter 615 provides for measuring actual radiation dosage applied, perhaps over multiple treatments. A multi-dimensional dosage map may be created from the output of the scintillator of the active catheter by use of the data acquisition system, for example.

The principles of the invention may also be employed in permanent seed implantation procedures since knowing the dose distribution within a patient prior to releasing the seed into the body provides physicians with the ability to modify the dose. For example, by monitoring the radiation source within a catheter or other delivery device being used during implantation prior to the source reaching the end of the device enables the physician to modify placement or dose, as appropriate.

Also, a seed implantation gun may also be employed as the delivery device in therapy seed implantation. The implantation gun may also include scintillating radiation detection materials arranged and configured according to principles of the invention.

Figure 7:
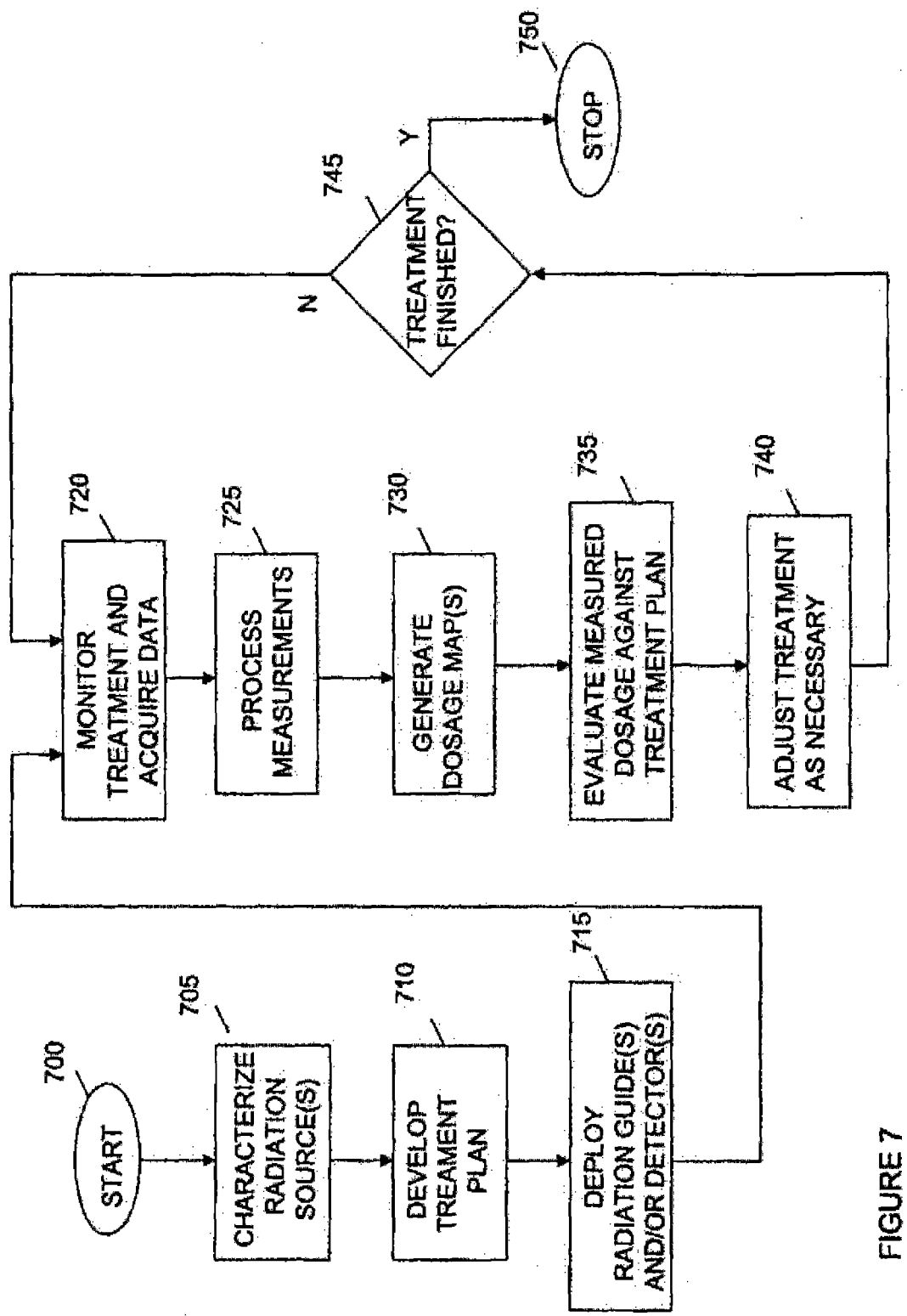
FIG. 7 is a flow diagram of an embodiment showing process steps of using an embodiment of the invention.

FIG. 7 is a flow diagram of an embodiment showing process steps of using an embodiment of the invention, beginning at step 700. FIG. 7 and all other flow diagrams herein may equally represent a high-level block diagram of components of the invention implementing the steps thereof. The steps of FIG. 7 may be implemented on computer program code in combination with the appropriate hardware. This computer program code may be stored on storage media such as a diskette, hard disk, CD-ROM, DVD-ROM or tape, as well as a memory storage device or collection of memory storage devices such as read-only memory (ROM) or random access memory (RAM). Further, the computer code may also be embodied, at least in part, in a medium such as a carrier wave, which can be extracted and processed by a computer. Additionally, the computer program code and any associated parametric data can be transferred to a workstation over the Internet or some other type of network, perhaps encrypted, using a browser and/or using a carrier wave.

Continuing at step 705, one or more radiation source(s) may be characterized which may include the use of scintillating material radiation detectors. At step 710, a treatment plan may be developed to administer radiation, typically based in part on data from the characterized radiation source(s). At step 715, one or more active catheters guides or other radiation delivery devices may be deployed along with any other radiation detector(s) according to the treatment plan. The configuration of the active catheters and/or radiation detectors may be confirmed by imaging techniques such as x-rays. At step 720, the treatment may be monitored in real-time by a data acquisition system which acquires outputs from the active catheter(s) and/or radiation detectors. At step 725, the outputs from the active catheters and/or detectors may be processed in real-time to account for physics of the treatment and to provide feedback on measured radiation levels to the physicians or technicians overseeing the treatment.

At step 730, a dosage map may be generated to show a two or three dimensional view of administered radiation. At step 735, an evaluation of measured dosage during treatment against expectations of the treatment plan may be made. This may be performed automatically by computer or by visual evaluation by the physicians or technicians. At step 740, the treatment may be adjusted as necessary to modify dosage levels which may include altering directionality or dwelling times, for example. This may be done automatically by computer control or by intervention by a physician or technician, depending on the nature of the necessary adjustments. At step 745, a check is made whether the treatment is finished which may depend on meeting the treatment plan goals or perhaps based on unexpected measured levels, for example. If the treatment is deemed finished, the process ends at step 750; otherwise, the treatment continues at step 720.

FIG. 8 is a diagram of an embodiment for external beam quality assurance, configured according to principles of the invention. A beam delivery system or apparatus 805 such as an external beam delivery apparatus may impart a beam of particles 810, such as photon, electron, proton, ion or hadron particles, upon a scintillating material 815 array which may comprise scintillating fibers for example, as a beam spot 820, that may pass through 825 the scintillating material 815. The scintillating material may generate signals in a beam's presence for providing a basis to calibrate the configuration, pattern and/or intensity of the incident beam 810.

In another aspect, the scintillating material 820 may be arranged as a plurality of arrays in two or more dimensions to form a combined array for achieving dose measurements at a point or plurality of points on the combined arrays. For example, but not limiting to this configuration, two fiber arrays may be arranged adjacent but the fibers in each adjacent array being perpendicular to one another (see, e.g., arrangement shown in FIG. 9B) so that a beam intensity measurement at one or more x-y locations may be acquired.

Figure 9A:
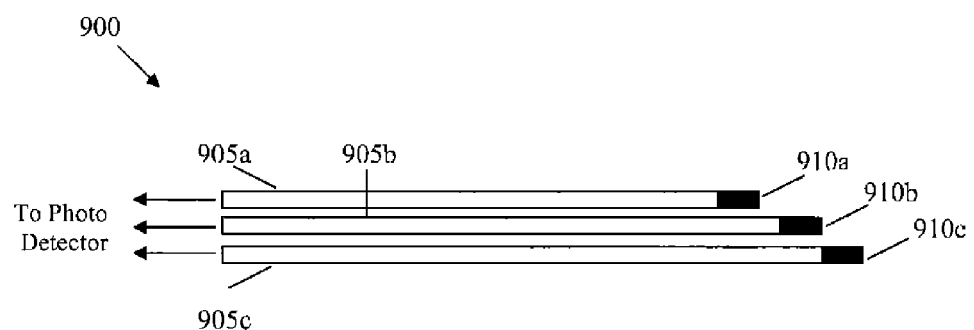
FIG. 9A is an illustration of a radiation detector scheme configured to permit determination of a dose, configured according to principles of the invention.

FIG. 9A is an illustration of a radiation detector scheme configured to permit determination of a dose, configured according to principles of the invention, generally denoted by reference numeral 900. A plurality of detectors 905a, 905b, 905c, which may be optical fibers with scintillating material 910a, 910b, 910c at one end of the respective detectors 905a, 905b, 905c for example, may be arranged proximate to each other so that they are at different relative lengths respective to one another, or at least the scintillating material 910a, 910b, 910c may be positioned at known relative locations from one another. This detector scheme 900 may be an array of detectors preconfigured with predetermined relative positions to one another, perhaps as a unified array of detectors held in fixed relationship to one another. The detectors 905a, 905b, 905c may be configured to be coupled to one or more photo detectors (not shown). When used in vivo, the level of radiation detected by each detector 905a, 905b, 905c may be used to determine a dosage amount at a given location(s), and/or may be used to develop a dosage map. In yet another configuration, the scintillating material 910a, 910b and 910c may be configured so that a dosage amount and/or location may be determined by subtracting levels from two scintillating material devices of differing lengths.

Figure 9B:
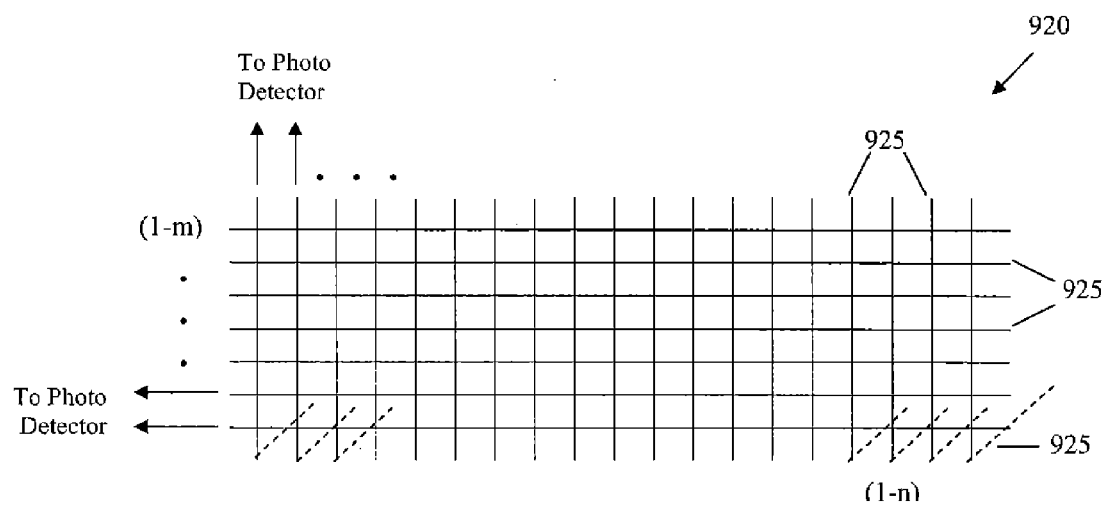
FIG. 9B is an illustration of an embodiment of a radiation detector configured to permit determination of a radiation dose or to map radiation, according to principles of the invention.

FIG. 9B is an illustration of an embodiment of radiation detectors configured to permit determination of a radiation dose or to map radiation, according to principles of the invention, generally denoted by reference numeral 920. A plurality of radiation detectors 925 may be arranged in the y-axis (1-*n*) and a plurality of radiation detectors 925 may be arranged in the x-axis (1-*m*) as shown. The plurality of radiation detectors 925 may comprise scintillating material and configured to be connectable to photo detectors. The 2-dimensional aspect of this configuration provides for determination of a radiation dose or to map radiation, since radiation levels may be associated with one or more particular x-y intersections. In another aspect, another set of detectors may be arranged in a z-axis (1-*n*) to provide a 3-dimensional detector. At least one first signal from a first subset of detectors in one axis and at least one second signal from a second subset of detectors in another axis (and optionally at least one third signal from a third subset of detectors in yet another axis) may provide a basis for producing a radiation map. The first subset of detectors and the second subset of detectors, and optionally a third subset of detectors, may be configured at an angle from one another. In one aspect the angle may be about ninety degrees, however, other angles may be employed.

Figure 10:
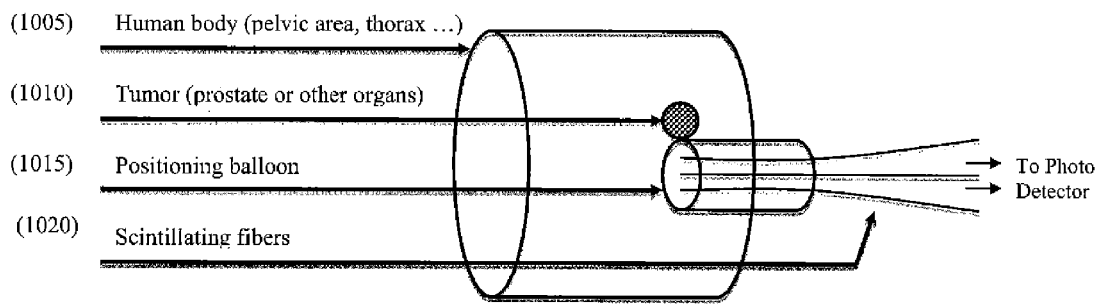
FIG. 10 is an exemplary schematic of a positioning balloon with one or more scintillating fibers as an in-vivo or ex-vivo dosimetry for quality monitoring, according to principles of the invention.

FIG. 10 is an exemplary schematic of a positioning balloon with one or more scintillating fibers as an in-vivo or ex-vivo dosimetry for quality monitoring, according to principles of the invention. An exemplary body location 1005, such as a pelvic area or thorax area, may encompass a tumor 1010 (perhaps related to a body organ like a prostate, for example). A positioning balloon 1015, commonly employed in surgical procedures, may be used to position one or more scintillating detectors 1020 such as scintillating fibers so that the scintillating detectors 1020 may be positioned in a desired location relative to the tumor to receive radiation for treatment or imaging. In this way, the radiation target, i.e., tumor 1010, may be held in mutual relative location with the scintillating detectors 1020, for receiving of external radiation treatment, for example.

Figure 11A:
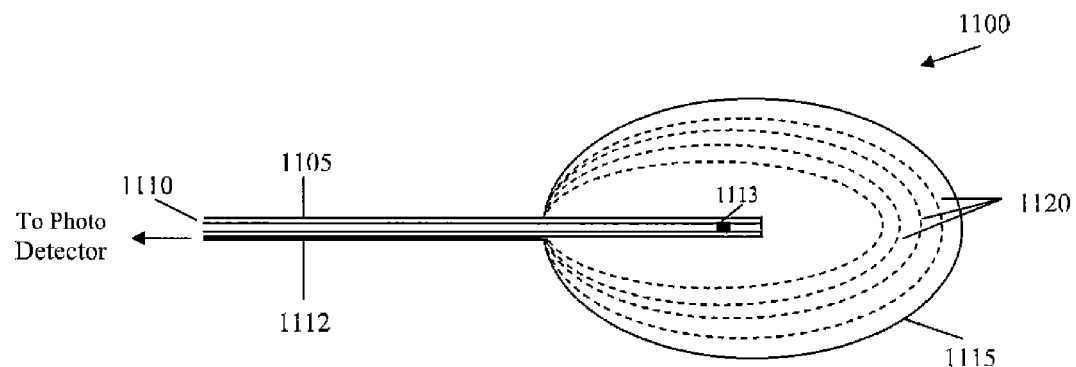
FIG. 11A is an exemplary embodiment of a flexible radiation detector, configured according to principles of the invention.

FIG. 11A is an exemplary embodiment of a flexible radiation detector, configured according to principles of the invention, generally denoted by reference numeral 1100. The flexible radiation detector 1100 comprises a catheter portion 1105 with a hollow portion 1110 (a receptacle) running along the length of the catheter portion 1105, providing essentially an enhanced balloon or similar catheter. A flexible or semi-rigid balloon portion 1115 attached at one end of the catheter portion 1105 may expand during a procedure perhaps using saline solution, for example. One or more scintillating fibers 1120 may be arranged within or upon the wall of the balloon portion 1115 and configured to conform to the contour of the balloon portion 1115 when expanded. The one or more scintillating fibers 1120 may be connected to a photo detector, perhaps via one or more connecting portions 1112 running along the catheter portion 1105. A radiation source 1113 may be inserted into the catheter portion 1105 into the balloon portion 1115 during treatment or imaging procedures, while the scintillating fibers 1120 may detect radiation levels/dosage during such treatment or imaging procedure, the principles described previously.

Figure 11B:
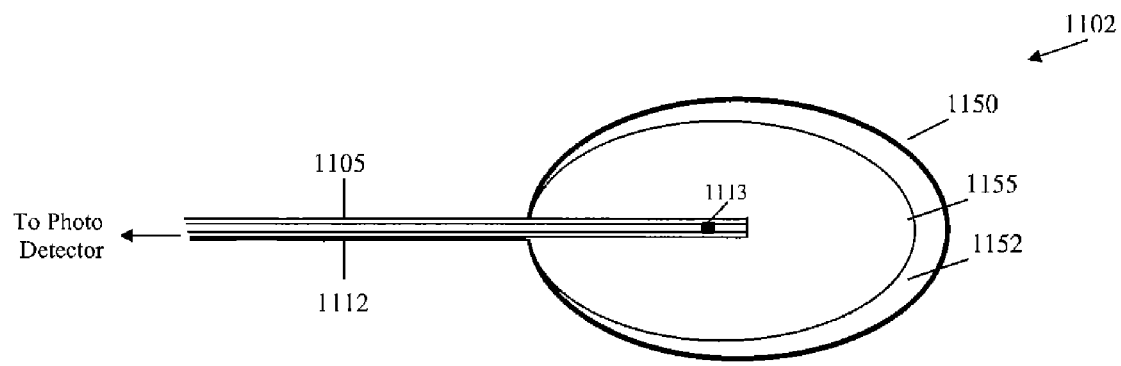
FIG. 11B is an exemplary embodiment of a flexible radiation detector, configured according to principles of the invention.

FIG. 11B is an exemplary embodiment of a flexible radiation detector, configured according to principles of the invention, generally denoted by reference numeral 1102. In this embodiments 1102, a second balloon portion 1155 may be configured inside of an outer balloon portion 1150. Scintillating material 1152 (e.g., liquid, solid or gas) may be contained within the two balloon portions 1150, 1155. Connecting portion 1112 may convey signals emitted by the scintillating material 1152 along the catheter portion 1105 to a photo detector. A radiation source 1113 may be inserted into the catheter portion 1105 to provide radiation treatment or, alternatively, an external beam delivery system (such as in reference to FIG. 8) could deliver the radiation beam, while the scintillating material 1152 provides dosage level signals. Moreover, in one aspect, any of the at least one balloon portion, e.g., portions 1150, 1155, may include the arrangement of FIG. 11A, i.e., scintillating materials arranged along the surface of, or embedded within, the balloon portion. In one aspect, the scintillating material 1152 may be configured into specific known partitions so that the signals from the partitions may be correlated to specific regions of the balloon portion.

Any of the scintillating radiation detectors described herein may be used to detect and measure dose from external beam or any other radiation therapy delivery system. The scintillating radiation detectors described herein may be used to measure dose from imaging devices, such as x-rays, CT scans, fluoroscopy, positron emission tomography (PET), CT, single photon emission computed tomography (SPECT), diagnostic scans, cardiac, for example. The scintillating detectors herein may also be used to measure a dose from beam delivery systems (imaging, radiotherapy and the like). To accomplish the above, the scintillating detectors may be placed externally (on the skin or an immobilization device, for instance) or internally (in a positioning balloon or catheter, for instance). The scintillation radiation detectors may also be used for beam profile checks such as for calibrating beam shapes and/or intensity ex vivo for external beam imaging devices. Any of the scintillating radiation detectors described herein may be used to alter a treatment plan.

For dosimeter detectors comprising scintillating fibers, signal degradation along the fiber length may be used to ascertain a position and/or directionality of the detected radiation. Here, in this example, smaller signals correspond, in a calculable way, to longer distance of travel along the fiber and, hence, position. Alternatively, by using a subtraction technique involving for instance two coupled fibers of slightly different lengths, a dose at a small or defined region may be calculated by subtracting the (possibly integrated) signal from the shorter from the signal from the longer, hence isolating the remaining subtracted dose to that deposited in the spatial region of fiber length difference. The dose evaluated would then be for the (presumably small) region of differing length only.

The external radiation types herein may include radiation related to treatment x-rays, electron beams, hadron beams, and the like, as well as to diagnostic modalities such as x-ray fluoroscopy, molecular imaging scans, SPECT, CT scans, and the like.

Various modifications and variations of the described methods and systems of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in the art are intended to be within the scope of the following claims.

What is claimed:

1. A radiation detector comprising:
   a catheter configured with a hollow portion extending along a length of the catheter and configured with at least one expandable portion; and
   scintillating material, wherein the scintillating material is arranged in a continuous manner along a perimeter of a wall of the at least one expandable portion or arranged along a length of the hollow portion from a location within the expandable portion to a location outside of the expandable portion, the scintillating material configured to be coupled to a photo detector for detecting incident levels of radiation in a therapy procedure, wherein the scintillating material comprises only one of: a scintillating gas, a scintillating liquid and a scintillating solid.

2. The radiation detector of claim 1, wherein the at least one expandable portion comprises a plurality of expandable portions, with at least one expandable portion configured within another expandable portion.

3. The radiation detector of claim 1, wherein the scintillating material comprises one or more scintillating fibers arranged along the surface of, or embedded within, at least one balloon portion.

4. The radiation detector of claim 1, wherein the hollow portion extends into the at least one expandable portion.

5. The radiation detector of claim 1, the hollow portion is configured to receive a radiation source.

6. The radiation detector of claim 5, wherein the scintillating material provides dosage level signals indicative of radiation from the radiation source.

7. The radiation detector of claim 1, further comprising the photo detector.

8. The radiation detector of claim 1, wherein the scintillating material is configured to conform to the contour of the at least one expandable portion, when expanded.

9. A radiation detector comprising:
an array of scintillating fibers to detect incident levels of radiation, the array configured to be insertable into a medical device, wherein the medical device is configured to be insertable into a patient for a medical procedure, and wherein each scintillating fiber of the array is configured to be individually coupled directly to a detector for measuring incident levels of radiation.

10. The radiation detector of claim 9, wherein the array of scintillating fibers is an independent component insertable into a catheter.

11. The radiation detector of claim 9, wherein the array of scintillation fibers is arranged to permit passage of a radiation source to be moved along the array.

12. The radiation detector of claim 11, wherein the array is configured as a circular array.

13. The radiation detector of claim 9, wherein the array of scintillation fibers is configured as a circular array to permit movement of a radiation source therewithin.

14. The radiation detector of claim 9, wherein the array of scintillation fibers comprises an independent component and the array comprises a plurality of individual fibers, wherein one or more individual fibers are removable.

15. The radiation detector of claim 9, wherein the array of scintillation fibers is arranged within an expandable balloon.

16. The radiation detector of claim 9, wherein the array of scintillation fibers is connectable to a detector for measuring incident levels of radiation.

17. The radiation detector of claim 9, wherein the medical device comprises a catheter.

18. The radiation detector of claim 1, wherein the scintillating material arranged in the continuous manner along a perimeter of a wall of the at least one expandable portion is arranged so that the scintillating material has a curved shape about the catheter, when the expandable portion is in the expanded state.

19. A radiation detector comprising:
an array of scintillating fibers to detect incident levels of radiation, the array configured to be insertable into a medical device, wherein the medical device is configured to be insertable into a patient for a medical procedure, wherein the array of scintillation fibers is arranged to permit passage of a radiation source to be moved along the array.

20. The radiation detector of claim 19, wherein the array is configured as a circular array.

21. A radiation detector comprising:
an array of scintillating fibers to detect incident levels of radiation, the array configured to be insertable into a medical device, wherein the medical device is configured to be insertable into a patient for a medical procedure, wherein the array of scintillation fibers is configured as a circular array to permit movement of a radiation source therewithin.

22. A radiation detector comprising:
an array of scintillating fibers to detect incident levels of radiation, the array configured to be insertable into a medical device, wherein the medical device is configured to be insertable into a patient for a medical procedure, wherein the array of scintillation fibers comprises an independent component and the array comprises a plurality of individual fibers, wherein one or more individual fibers are removable.

23. A radiation detector comprising:
an array of scintillating fibers to detect incident levels of radiation, the array configured to be insertable into a medical device, wherein the medical device is configured to be insertable into a patient for a medical procedure, wherein the array of scintillation fibers is arranged within an expandable balloon.

* * * * *